United States Patent [19]

Kosley, Jr. et al.

[11] Patent Number: 4,666,904
[45] Date of Patent: May 19, 1987

[54] AMINOACYLLABDANES, PHARMACUETICAL COMPOSITIONS AND USE

[75] Inventors: Raymond W. Kosley, Jr., Bridgewater; Robert J. Cherill, Somerset, both of N.J.

[73] Assignee: Hoechst-Roussel Pharmaceuticals Inc., Somerville, N.J.

[21] Appl. No.: 920,547

[22] Filed: Oct. 20, 1986

Related U.S. Application Data

[60] Division of Ser. No. 804,405, Dec. 4, 1985, Pat. No. 4,639,446, which is a continuation-in-part of Ser. No. 681,779, Dec. 14, 1984, abandoned.

[51] Int. Cl.[4] .................... A61K 31/36; A61K 31/54; C07D 493/02; C07D 497/02
[52] U.S. Cl. .................... 514/222; 514/231; 514/236; 514/252; 514/321; 514/365; 514/374; 514/397; 514/422; 514/439; 514/453; 544/58.2; 544/58.7; 544/145; 544/148; 544/378; 546/197; 548/146; 548/215; 548/336; 548/526; 549/31; 549/229
[58] Field of Search .................... 544/58.2, 58.7, 145, 544/148, 378; 546/197; 548/146, 215, 336, 526; 514/222, 231, 236, 252, 321, 365, 374, 397, 422, 439, 453; 549/31, 229

[56] References Cited

U.S. PATENT DOCUMENTS 4,517,200 5/1985 Kreutwer et al. .................. 514/455

Primary Examiner—Robert W. Ramsuer
Attorney, Agent, or Firm—Raymond R. Wittekind

[57] ABSTRACT

Novel aminoacyllabdanes, intermediates and processes for the preparation thereof, and methods for reducing intraocular pressure utilizing compounds or compositions thereof are disclosed.

8 Claims, No Drawings

AMINOACYLLABDANES, PHARMACUETICAL COMPOSITIONS AND USE

This is a division of application Ser. No. 804,405 filed Dec. 4, 1985 now U.S. Pat. No. 4,639,446 which is a continuation-in-part of application Ser. No. 681,779, filed Dec. 14, 1984, now abandoned.

The present invention relates to aminoacyllabdanes. More particularly, the present invention relates to aminoacyllabdanes of Formula 1

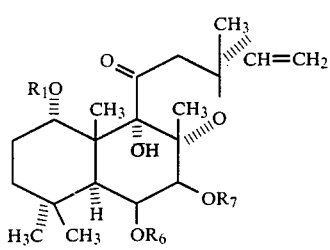

wherein $R_1$ is $R_2R_3NCHR_4CO$ wherein $R_2$ is hydrogen, loweralkyl or benzyl, $R_3$ is hydrogen or loweralkyl and $R_4$ is hydrogen, loweralkyl or benzyl; $R_2$ and $R_3$ taken together with the nigrogen atom to which they are attached form a group of the formula

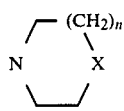

wherein X is CO, O, S, SO, $SO_2$; a group of the formula $CHR_9$ wherein $R_9$ is hydrogen, loweralkyl or a group of the formula $OR_{10}$ wherein $R_{10}$ is hydrogen or $COR_{11}$ wherein $R_{11}$ is loweralkyl; or a group of the formula $NR_{12}$ wherein the $R_{12}$ is loweralkyl; n is 0 or 1; $R_6$ is hydrogen or a group of the formula $R_5CO$ wherein $R_5$ is hydrogen or loweralkyl; $R_7$ is hydrogen or a group of the formula $R_8CO$ wherein $R_8$ is hydrogen or loweralkyl; and $R_6$ and $R_7$ taken together form a group of the formula CO or SO; the optical and geometric isomers thereof, or a pharmaceutically acceptable acid addition salt thereof, which are useful for reducing intraocular pressure, alone or in combination with inert adjuvants.

Subgeneric to the aminoacyllabdanes of the present invention are compounds of formula 1 wherein:

(a) $R_2$ and $R_3$ are hydrogen or loweralkyl;
(b) $R_2$ is hydrogen and $R_3$ is loweralkyl;
(c) $R_2$ and $R_3$ taken together with the nitrogen atom to which they are attached form a group of the formula

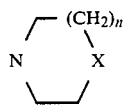

wherein X is CO, O, S, SO, $SO_2$; a group of the formula $CHR_9$ wherein $R_9$ is hydrogen, loweralkyl or a group of the formula $OR_{10}$ wherein $R_{10}$ is hydrogen or $COR_{11}$ wherein $R_{11}$ is loweralkyl; or a group of the formula $NR_{12}$ wherein $R_{12}$ is loweralkyl; and n is 0 or 1;

(d) $R_4$ is hydrogen or loweralkyl;

(e) $R_4$ is benzyl;
(f) $R_6$ and $R_7$ taken together form a group of the formula CO or SO;
(g) $R_6$ is hydrogen or a group of the formula $R_5CO$ wherein $R_5$ is hydrogen or loweralkyl; and
(h) $R_7$ is hydrogen or a group of the formula $R_8CO$ wherein $R_8$ is hydrogen or loweralkyl.

The present invention also relates to compounds of formula 2

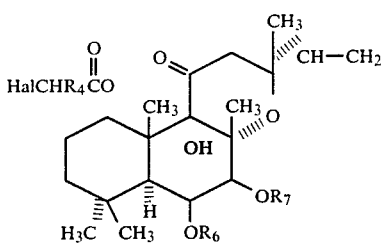

wherein $R_4$ is hydrogen, loweralkyl or benzyl; $R_6$ is hydrogen or a group of the formula $R_5CO$ wherein $R_5$ is hydrogen or loweralkyl; $R_7$ is hydrogen or a group of the formula $R_8CO$ wherein $R_8$ is hydrogen or loweralkyl; Hal is chloro or bromo; or the optical and geometric isomers thereof, which are useful as intermediates for the preparation of the aminoacyllabdanes of the present invention.

A compound of formula 2 wherein Hal is bromo is preferred.

As used through the specification and appended claims, the term "aklyl" refers to a straight or branched chain hydrocarbon radical containing no unsaturation and having 1 to 8 carbon atoms such as methyl, ethyl, 1-propyl, 2-propyl, 2-methylpropyl, 1-pentyl, 2-pentyl, 3-hexyl, 4-heptyl, 2-octyl, and the like; the term "alkanol" refers to a compound formed by a combination of an alkyl group and a hydroxy radical. Examples of alkanols are methanol, ethanol, 1- and 2-propanol, 1,2-dimethylethanol, hexanol, octanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid and the like; the term "halogen" refers to a member of the family consisting of fluorine, chlorine, bromine or iodine. The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl and the like. The term "lower" as applied to any of the aforementioned groups refers to a group having a carbon skeleton containing up to and including 6 carbon atoms.

In the formulas presented herein the various substitutents are illustrated as joined to the labdane nucleus by one of two notations: a solid line (—) indicating a substituent which is in the $\beta$-orientation (i.e., above the plane of the molecule) and a broken line ( ----- ) indicating a substituent which is in the $\alpha$-orientation (i.e., below the plane of the molecule). The formulas have all been drawn to show the compounds in their absolute stereochemical configuration. Inasmuch as the starting materials having a labdane nucleus are naturally occurring or are derived from naturally occurring materials, they, as well as the final products, have a labdane nucleus existing in the single absolute configuration depicted herein. The processes of the present invention, however, are intended to apply as well to the synthesis of labdanes of the racemic series.

In addition to the optical centers of the labdane nucleus, the substituents thereon may also contain chiral centers contributing to the optical properties of the compounds of the present invention and providing a means for the resolution thereof by conventional methods, for example, by the use of optically active acids. The present invention comprehends all optical isomers and racemic forms of the compounds of the present invention, where such compounds have chiral centers in addition to those of the labdane nucleus.

The novel aminoacyllabdanes of the present invention are synthesized by the processes illustrated in the Reaction Scheme.

To prepare an aminoacyllabdane 4 wherein $R_7$ is alkanoyl, a 1-hydroxylabdane 3 wherein $R_7$ is alkanoyl is acylated with a haloalkylcarbonyl halide of formula 8

HalCHR$_4$COHal              8 wherein $R_4$ and Hal are as hereinbeforedescribed to provide a 1-haloalkanoyloxyladane 2 which is condensed with an amine of formula 9

$R_2R_3NH$              9 to afford 4.

The acylation of hydroxylabdane 3 is readily accomplished by treating a hydroxylabdane 3 with a haloalkylcarbonyl halide 8 such as a bromoalkylcarbonyl bromide or a chloroalkylcarbonyl chloride, a bromoalkylcarbonyl bromide being preferred, in a halocarbon in the presence of a tertiary amine. Among halocarbons, there may be mentioned dichloromethane, trichloromethane, 1,1- and 1,2-dichloromethane and 1,1- and 1,2-dichloroethene. Dichloromethane is the preferred halocarbon. Among tertiary amines, there may be mentioned, for example, 4-dimethylaminopyridine and N,N-dimethylaniline. N,N-Dimethylaniline is the preferred amine. While the temperature at which the acylation is performed is not narrowly critical, it is preferred to conduct the reaction at a temperature within the range of about $-0°$ to about 50° C. It is most preferred to perform the acylation at a temperature within the range of about 0° to about 25° C.

The condensation is effected by treating a haloalkanoyloxylabdane 2 with a primary or secondary amine 9 in and alkyl alkanoate or halocarbon, or a mixture thereof. Included among alkyl alkanoates are methyl acetate, ethyl acetate and ethyl propanoate. Included among halocarbons are dichloromethane, trichloromethane, 1,1- and 1,2-dichloromethane. Ethyl acetate and dichloromethane are the preferred solvents. The condensation is preferably performed in the absence of added base. An alkali metal bicarbonate such as lithium, sodium or potassium bicarbonate may, however, be utilized. The condensation temperature is not critical. The conversion proceeds readily at a temperature within the range of about 0° to about 50° C. A reaction temperature of about 25° C. is preferred.

To provide an aminoacyllabdane 5 wherein $R_6$ is alkanoyl, aminoacyllabdane 4 may be rearranged, for example, by treating 4 with lithium, 1,1,1,3,3,3-hexamethyldisilazide in an ethereal solvent such as tetrahydrofuran at a temperature of about 0° C.

To provide an aminoacyllabdane 6 having free 6$\beta$,$\beta$-hydroxy groups, one may treat 1$\alpha$, 6$\beta$,7$\beta$,9$\alpha$-tetrahydroxylabdane 3 wherein $R_7$ is hydrogen with a haloalkylcarbonyl halide 8 under reaction conditions substantially similar to those employed for the conversion of trihydroxylabdane 3 wherein $R_7$ is alkanoyl to aminoacylabdane 4 wherein $R_7$ is alkanoyl.

To synthesize an aminoacyllabdane 8 wherein $R_6$ and $R_7$ are alkanoyl, one may acylate an aminoacyllabdane 5 with an alkanoic acid of formula 10

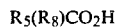

$R_5(R_8)CO_2H$              10 wherein $R_5$ and $R_8$ are as hereinbeforedescribed, an anhydride thereof of formula 11

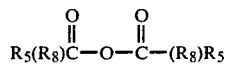

$$R_5(R_8)\overset{O}{\overset{\|}{C}}-O-\overset{O}{\overset{\|}{C}}-(R_8)R_5 \qquad 11$$

wherein $R_5$ and $R_8$ are as hereinbeforedescribed, or mixtures thereof, or the halide thereof of formula 12

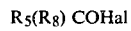

$R_5(R_8)$ COHal              12 wherein $R_5$, $R_8$ and Hal are as hereinbeforedescribed. The acylation may be performed in the presence of a basic catalyst such as, for example, pyridine, lutidine or collidine at a reduced temperature within the range of about 0° to 25° C.

In the event a carboxylic acid of formula 10 is employed in the acylation step, a carbodiimide such as, for example, dicyclohexylcarbodiimide, may be utilized.

Aminoacyllabdanes of formula 7 wherein Y is CO or SO may be prepared by treating a dihydroxylabdane 6 with a compound of formula 13

Hal-Y-Hal              13 wherein Y is CO or SO and Hal is as hereinbeforedescribed in the presence of an aromatic amine such as pyridine, lutidine or s-collidine at a reduced temperature of about $-10°$ to about 10° C.

The labdane starting materials for the processes of the present invention, i.e., labdanes of formula 3 wherein $R_7$ is hydrogen or a group of the formula $R_8CO$ wherein $R_8$ is hydrogen or alkyl, are described in U.S. Pat. No. 4,134,986, issued Jan. 16, 1979 to B. S. Bajwa, et al.

The aminoacyllabdanes of the present invention are useful in the treatment of elevated intraocular pressure by virtue of their ability to reduce intraocular pressure as determined by the method described by J. Caprioli, et al., *Invest. Ophthalmol. Vis. Sci.*, 25, 268 (1984). The results of the determination expressed as percent decrease of outflow pressure is presented in the Table.

TABLE

| COMPOUND | CONCEN-TRATION (%) | DECREASE IN OUT-FLOW PRESSURE (%) |
|---|---|---|
| 7$\beta$-acetoxy-8,13-epoxy-1$\alpha$-diethylaminoacetoxy-6$\beta$,9$\alpha$-dihydroxylabd-14-en-11-one | 1.0<br>0.1 | 66<br>30 |
| 7$\beta$-acetoxy-8,13-epoxy-1$\alpha$-[(morpholin-4-yl)acetoxy-6$\beta$,9$\alpha$-dihydroxylabd-14-en-11-one | 1.0 | 63 |
| 7$\beta$-acetoxy-8,13-epoxy-1$\alpha$,6$\beta$,9$\alpha$-trihydroxylabd-14-en-11-one | 1.0<br>0.1 | 51<br>23 |

Intraocular pressure reduction is achieved when the present aminoacyllabdanes are administered to a subject requiring such treatment as an effective topical dose of a 0.01 to 3.0% solution or suspension. A particularly effective amount is about 3 drops of a 1% preparation per day. It is to be understood, however, that for any particular subject, specific dosage regimens should be adjusted according to the individual need and the professional judgement of the person administering or supervising the administration of the aforesaid compound. It is to be further understood that the dosages set forth herein are exemplary only and that they do not, to any extent, limit the scope or practice of the invention.

Compounds of the present invention include:

(a) 7β-Acetoxy-1α-(2-aminopropionyloxy)-8,13-epoxy-6β,9α-dihydroxylabd-14-en-11-one;

(b) 7β-Acetoxy-1α-[2-(N-benzylamino)propionyloxy]-8,13-epoxy-6β,9α-dihydroxylabd-14-en-11-one;

(c) 7β-Acetoxy-8,13-epoxy-1α-[2-(N-ethylamino)propionyloxy]-6β,9α-dihydroxylabd-14-en-11-one;

(d) 7β-Acetoxy-8,13-epoxy-1α-[2-(N-ethylamino)-3-phenylpropionyloxy]-6β,9α-dihydroxylabd-14-en-11-one;

(e) 6β-Acetoxy-8,13-epoxy-7β,9α-dihydroxy-1α-(dimethylaminoacetoxy)labd-14-en-11-one;

(f) 7β-Acetoxy-8,13-epoxy-6β-formyloxy-9α-hydroxy-1α-(dimethylaminoacetoxy)labd-14-en-11-one;

(g) 8,13-Epoxy-7β-formyloxy-6β,9α-dihydroxy-1α-(dimethylaminoacetoxy)labd-14-en-11-one;

(h) 8,13-Epoxy-6β,7β,9-trihydroxy-1α-(dimethylaminoacetoxy)labd-14-en-11-one carbonate;

(i) 8,13-Epoxy-6β,7β, 9α-trihydroxy-1α-(dimethylaminoacetoxy)labd-14-en-11-one sulfite.

The aminoacyllabdanes of the present invention are also useful in the treatment of hypertension, congestive heart failure, bronchial asthma and psoriasis.

Effective amounts of the compounds of the present invention may be administered to a subject by any one of various methods, for example, orally as in capsules or tablets, parenterally in the form of sterile solutions or suspensions, in some cases intravenously in the form of sterile solutions, or suspensions, and topically in the form of solutions, suspensions or ointments, and by aersol spray. The aminoacyllabdanes of the present invention, while effective themselves, may be formulated and administered in the form of their pharmaceutically acceptable addition salts for purposes of increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, citric acid and the like.

Effective quantities of the compounds of the invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compounds, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 0.1–30 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral or topical therapeutic administration, the active compounds of the invention may be incorporated into a solution, suspension, ointment or cream. These preparations should contain at least 0.01% of active compound, but may be varied between 0.5 and about 5% of the weight thereof. The amount of active compounds in such compositions is such that a suitable dosage will be obtained. Preferred compositions and preparations according to the present invention are prepared so that a parenteral or topical dosage unit contains between 0.01 to 10 milligrams of active compound.

The solutions or suspensions for topical or parenteral administration may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules or disposable syringes; the topical preparation may be enclosed in multiple dose vials or dropping bottles, made of glass or plastic.

All temperatures are given in degrees Centigrade.

EXAMPLE 1

7β-Acetoxy-8,13-epoxy-1α-(diethylaminoacetoxy)-6β-9α-dihydroxylabd-14-en-11-one hydrochloride To 200 mg of 7β-acetoxy-8,13-epoxy-1α,6β,9α-trihydroxylabd-14-en-11-one was added a solution of 0.70 ml of N,N-dimethylaniline in 1 ml of dry (3A molecule sieves) dichloromethane. The solution, under nitrogen, was cooled in an ice bath. To the solution was added slowly, dropwise, a solution of 0.050 ml of bromoacetyl bromide. The mixture was stirred 2 hrs at ice bath temperature and 1 hr at room temperature. The mixture was diluted with ethyl acetate, washed with sodium bicarbonate solution and water, and dried over anhydrous sodium sulfate. Filtration followed by evaporation of the solvent provided an oil. The oil was dissolved in 3 ml of ethyl acetate. To the solution was added 0.068 mg of sodium bicarbonate and a solution of 0.050 ml of diethylamine in 1 ml of ethyl acetate. The mixture was stirred 0.5 hr at 80°, allowed to cool to room temperature and filtered. The filtrate was diluted with ethyl acetate, washed with water, saturated sodium chloride solution and dried over anhydrous sodium sulfate. Filtration followed by evaporation of solvent provided an oil. The oil was dissolved in a minimum volume of 70/30 hexane/ethyl acetate and chromatographed on 50 g of silica gel (230–400 mesh, nitrogen pressure, eluent: 30×15 ml of 70/30 hexane/ethyl acetate). The appropriate fractions were concentrated and the solvent evaporated to provide 129 mg (50.5%) of product as an oil. The hydrochloride was precipitated/crystallized from ether to provide product as the hydrochloride, mp 160°–165°.

Analysis: Calculated for $C_{28}H_{45}NO_8$ HCl: 60.04%C, 8.28%H, 2.50%N, Found: 59.79%C, 7.93%H, 2.44%N.

EXAMPLE 2

7β-Acetoxy-8,13-epoxy-1α-(dimethylaminoacetoxy)-6β,9α-dihydroxylabd-14-en-11-one hydrochloride To 100 mg of 7β-acetoxy-8,13-epoxy-1α, 6β,9α-trihydroxylabd-14-en-11-one was added a solution of 0.035 ml of N,N-dimethylaniline in 1 ml of dry dichloromethane. The solution was cooled in an ice bath. To the solution was added slowly, dropwise, a solution of 0.025 ml of bromoacetyl bromide in 1 ml of dry dichloromethane. The mixture was stirred 1 hr at ice bath temperature and allowed to warm to room temperature. The mixture was diluted with ethyl acetate, washed with sodium bicarbonate solution, water and dried over anhydrous sodium sulfate. Filtration followed by evaporation of the solvent provided an oil. The oil was dissolved in 2 ml of ethyl acetate. To the solution was added 1 ml of ethyl acetate which had been saturated with dimethylamine (gas). The solution was stirred at room temperature for 15 min, diluted with ethyl acetate, washed with sodium bicarbonate solution, saturated sodium chloride solution and dried over anhydrous sodium sulfate. Filtration followed by evaporation of solvent provided an oil. The oil was chromatographed on silica gel (20 g, 230–400 mesh; eluent: 50×15 ml of 70/30 hexane/ethyl acetate). Evaporation of the appropriate fractions provided 93 mg (76.6%) of product as an oil, which upon addition of ethereal hydrogen chloride, precipitated the hydrochloride, mp 156°–182°.

Analysis: Calculated for $C_{26}H_{41}NO_8$ HCl: 58.69%C, 7.69%H, 2.63%N, Found: 58.55%, 8.06%H, 2.56%N.

EXAMPLE 3

7β-Acetoxy-8,13-epoxy-1α-[(pyrrolidin-1-yl)]acetoxy]-6β,9α-dihydroxylabd-14-en-11-one hydrochloride To a stirred solution of 100 mg of 7β-acetoxy-8,13-epoxy-1α,6β,9α-trihydroxylabd-14-en-11-one in 1 ml of dry dichloromethane and 0.035 ml of N,N-dimethylaniline at 0°, under nitrogen, was added dropwise a solution of 0.025 ml of bromoacetyl bromide in 1 ml of dry dichloromethane. The mixture was allowed to warm to room temperature, diluted with ethyl acetate, washed with sodium bicarbonate solution, water and dried over anhydrous sodium sulfate. The solution was filtered and concentrated to an oil. The oil was dissolved in 3 ml of ethyl acetate and added to a stirred solution of 0.1 g of pyrrolidine in 1 ml of ethyl acetate. The mixture was stirred 0.5 hr at room temperature, diluted with ethyl acetate, extracted twice with ethyl acetate, washed three times with water, once with saturated sodium chloride solution, dried over sodium sulfate, filtered and the solvent evaporated to provide an oil. The oil was dissolved in a minimum volume of 70% ethyl acetate/hexane, and flashed chromatographed on 50 g of silica gel (230–400 mesh; 75×15 ml). Concentration of the appropriation fractions provided an oil. The oil was dissolved in anhydrous ether and the hydrochloride precipitated to provide 50.5 mg (37.1%) of product, mp 148–158.

Analysis: Calculated for $C_{28}H_{43}NO_8$ HCl: 60.25%C, 7.95%H, 2.51%N, Found: 60.64%C, 8.29%H, 2.50%N.

EXAMPLE 4

7β-Acetoxy-8,13-epoxy-1α-[(morpholin-4-yl)acetoxy]-6β,9α-dihydroxylabd-14-en-11-one hydrochloride To a stirred solution of 109 mg of 7β-acetoxy-8,13-epoxy-1α, 6β,9α-trihydroxylabd-14-en-11-one in 1 ml of dry dichloromethane containing 0.038 ml of dimethylaniline in an ice bath was added dropwise a solution of 0.029 ml of bromoacetyl bromide in one ml of dry dichloromethane. The mixture was stirred at ice bath temperature for one hr, diluted with ethyl acetate, washed with water, saturated sodium bicarbonate solution, water and dried over anhydrous sodium sulfate. Filtration followed by evaporation of solvent provided an oil which was dissolved in 2 ml of dry dichloromethane and added to a solution of 0.1 g of morpholine in 2 ml of ethyl acetate. The mixture was stirred 1 hr at room temperature, diluted with ethyl acetate, washed with water, saturated sodium bicarbonate solution, water and dried over anhydrous sodium sulfate. The solution was filtered and concentrated to an oil. The oil was dissolved in a minimum volume of 1/1 ethyl acetate/hexane and flash chromatographed on silica gel (230–400 mesh) (eluent: 20×15 ml of 1/1 ethyl acetate/hexane). The appropriate fractions were combined and concentrated to an oil. The oil was dissolved in ether and precipitated with ethereal hydrogen chloride to provide 67.3 mg (61.7%) of product as the hydrochloride, mp 153°–163°.

Analysis: Calculated for $C_{25}H_{43}NO_9$ HCl: 58.57%C, 7.73%H, 2.44%N, Found: 58.99%C, 7.69%H, 2.14%N.

EXAMPLE 5

7β-Acetoxy-8,13-epoxy-1α-[(di-n-propylamino)acetoxy]-6β,9α-dihydroxylabd-14-en-11-one hydrochloride To a stirred solution of 108 mg of 7β-acetoxy-8,13-epoxy-1α,9β,9α-trihydroxylabd-14-en-11-one in a solution of 1 ml of dry dichloromethane containing 0.038 ml of dimethylaniline, in an ice bath, under nitrogen, was added slowly dropwise a solution of 0.027 ml of bromoacetyl bromide in 1 ml of dry dichloromethane. The mixture was stirred at 0° for 1 hr, allowed to warm to room temperature, diluted with ethyl acetate, washed with cold water, saturated sodium bicarbonate solution and dried over anhydrous sodium sulfate. Filtration followed by evaporation of solvent provided an oil. The oil was dissolved in 1 ml of dichloromethane and added to a stirred solution of 0.1 g of di-n-propylamine in 1 ml of ethyl acetate. The solution was stirred 1 hr at room temperature and extracted with ether. The extracts were washed twice with water, once with saturated sodium chloride solution and dried over anhydrous sodium sulfate. Filtration followed by evaporation of solvent provided an oil. The oil was dissolved in a minimum volume of 20% ethyl acetate/hexane and flash chromatographed on 25 g of silica gel (230–400 mesh) (eluent: 25×10 ml of 20% ethyl acetate/hexane). Concentration of the appropriate fractions provided an oil. Addition of ethereal hydrogen chloride to an ethereal solution of the oil provided 59.9 mg (38.8%) of product as the hydrochloride, mp 199°–202°.

Analysis: Calculated for $C_{30}H_{49}NO_8HCl$: 61.26%C, 8.57%H, 2.38%N, Found: 61.08%C, 8.46%H, 2.26%N.

EXAMPLE 6

8,13-Epoxy-1-(diethylaminoacetoxy)-6β,7β,9α-trihydroxylabd-14-en-11-one hydrochloride A solution of 200 mg of 7β-acetoxy-8,13-epoxy-1α,6β,9α-trihydroxylabd-14-en-11-one in 10 ml of a sat potassium carbonate solution in 20% aqueous methanol was stirred 2 hr at 25°–28°. The mixture was diluted with ethyl acetate, washed twice with water, once with saturated sodium chloride solution, dried over anhydrous sodium sulfate, filtered and concentrated to provide 157 ml of 8,13-epoxy-1α,6β,7β,9α-tetrahydroxylabd-14-en-11-one as an oil.

To a stirred solution of 157 mg of 8,13-epoxy-1α,6β,7β,9α-tetrahydroxylabd-14-en-11-one, 0.0593 ml of N,N-dimethylaniline and 1 ml of dry dichloromethane in an ice bath, under nitrogen, was added dropwise a solution of 0.0421 ml of bromoacetyl bromide in 1 ml of dry dichloromethane. The mixture was stirred 1 hr at 0°, poured into ice water/ethyl acetate, washed with cold sat sodium bicarbonate solution, water and dried over anhydrous sodium sulfate. Filtration followed by evaporation of solvent provided an oil. The oil was dissolved in 1 ml of dry dichloromethane and added to a stirred solution of 0.1 g of diethylamine in 1 ml of ethyl acetate. The solution was stirred for 1 hr at ambient temperature and extracted with ethyl acetate. The extract was washed with water, saturated sodium chloride solution and dried over anhydrous sodium sulfate. Filtration followed by evaporation provided an oil. The oil was dissolved in a minimum volume of 1/1 ethyl acetate/hexane and flash chromatographed on 20 g of silica gel (230–400 mesh) (eluent: 25×10 ml of 1/1 ethyl acetate/hexane). Concentration of the appropriate fractions provided an oil, the hydrochloride of which was precipitated from ether to yield 90.2 mg (42.4%) of product, mp 127°–157°.

Analysis: Calculated for $C_{26}H_{43}NO_7HCl$: 60.27%C, 8.56%H, 2.70%N, Found: 59.99%C, 8.74%H, 2.58%N.

EXAMPLE 7

7β-Acetoxy-8,13-epoxy-1α-[(4-hydroxypiperidin-1-yl)acetoxy]-6β,9α-dihydroxylabd-14-en-11-one hydrochloride To a stirred solution of 106 mg of 7β-acetoxy-8,13-epoxy-1α,6β,9α-trihydroxylabd-14-en-11-one in 1 ml of dry dichloromethane containing 0.038 ml of dimethylaniline, in an ice bath, was added dropwise a solution of 0.027 ml of bromoacetyl bromide in 1 ml of dry dichloromethane. The mixture was stirred at 0° for 1 hr, allowed to warm to room temperature, poured onto ice sodium bicarbonate ethyl acetate, extracted with ethyl acetate, washed with water and dried over anhydrous sodium sulfate. Filtration followed by evaporation of solvent provided an oil which was dissolved in 1 ml of dichloromethane and added to a stirred solution of 0.10 g of 4-hydroxypiperidine in 1 ml of ethyl acetate. The mixture was stirred 1 hr at room temperature, poured onto ice/water ethyl acetate, extracted with ethyl acetate, washed with water, saturated sodium chloride solution and dried over anhydrous sodium sulfate. Filtration followed by evaporation of the solvent provided an oil. The oil was dissolved in a minimum volume of 30% ethyl acetate/hexane and flash chromatographed on 25 g of silica gel (230–400 mesh). Concentration of the appropriate fractions gave an oil. Treatment of the oil with ethereal hydrogen chloride gave 0.109 g (76.4%) of product as the hydrochloride, mp 166°–189°.

EXAMPLE 8

7β-Acetoxy-8,13-epoxy-1α-[(thiomorpholin-4-yl)acetoxy]-6β,9α-dihydroxylabd-14-en-11-one To a stirred solution of 104 mg of 7β-acetoxy-8,13-epoxy-1α,6β,9α-trihydroxylabd-14-en-11-one containing 0.037 ml of N,N-dimethylaniline in 1 ml of dry dichloromethane at 0° under nitrogen was added dropwise a solution of 0.026 ml of bromoacetyl bromide. The mixture was stirred 1 hr at 0°, allowed to warm to room temperature, poured onto ice, extracted with ethyl acetate, washed with anhydrous sodium sulfate, filtered, and the filtrate concentrated to an oil. The oil was dissolved in 1 ml of dry dichloromethane and the solution was added dropwise to a solution of 0.1 g of thiomorpholine in 1 ml of ethyl acetate. The mixture was stirred 1.5 hr, poured onto ice, diluted with ethyl acetate, washed with water, saturated sodium chloride and dried over anhydrous sodium sulfate. Filtration followed by evaporation of solvent and purification by flash chromatography to yield an oil. The oil was dissolved in ether and ethereal hydrogen chloride was added to provide 69.1 mg (47.8%) of product, as the hydrochloride, mp 161°–171°.

EXAMPLE 9

7β-Acetoxy-8,13-epoxy-1α-[(piperidin-1-yl)acetoxy]-6β,9α-dihydroxylabd-en-11-one hydrochloride To a stirred solution of 104 mg of 7β-acetoxy-8,13-epoxy-1α,6β,9α-trihydroxylabd-14-en-11-one in 1 ml of dry dichloromethane containing 0.037 ml of dimethylaniline in an ice bath, was added slowly, dropwise, a solution of 0.026 ml of bromoacetyl bromide in 1 ml of dry dichloromethane. The mixture was stirred for 1 hr at ice bath temperature, allowed to warm to room temperature, diluted with ethyl acetate, poured into ice/water, extracted with ethyl acetate, washed with cold, saturated sodium bicarbonate solution, water, and dried over anhydrous sodium sulfate. Filtration followed by evaporation of the solvent provided an oil which was dissolved in 1.5 ml of dichloromethane and added dropwise to a stirred solution of 0.1 g of piperidine in 1 ml of ethyl acetate. The mixture was stirred for 1.5 hr at room temperature. The solution was diluted with ethyl acetate, washed with water, saturated sodium chloride solution and dried over anhydrous sodium sulfate. Filtration followed by evaporation of solvent provided an oil. The oil was purified by flash chromatography on silica gel (230–400 mesh; eluent: 30% ethyl acetate/hexane). Evaporation of the solvent provided an oil, which as treated with ethereal hydrogen chloride to provide 34.8 mg (23.9%) of product, as the hydrochloride, mp 160°–184°.

Analysis: Calculated for $C_{28}H_{45}NO_8HCl$: 60.88%C, 8.10%H, 2.45%N, Found: 60.29%C, 7.93%H, 2.24%N.

EXAMPLE 10

7β-Acetoxy-8,13-epoxy-1α-(isopropylaminoacetoxy)-6β,9α-dihydroxylabd-14-en-11-one hydrochloride To a stirred solution of 0.0301 g of 7β-acetoxy-8,13-epoxy-1α,6β,9α-trihydroxylabd-14-en-11-one in a stirred solution of 3 ml of dry dichloromethane containing 0.106 ml of dimethylaniline at 0°, under nitrogen, was added dropwise a solution of 0.075 ml of bromoacetyl bromide in 3 ml of dry dichloromethane. The mixture was stirred 1 hr at 0°, poured into ice water, washed with ice cold sat sodium bicarbonate solution, water and dried over anhydrous sodium sulfate. Filtration followed by evaporation of solvent provided an oil. The oil was dissolved in 3 ml of dry dichloromethane and added dropwise to a stirred solution of 0.300 g of isopropylamine in 3 ml of ethyl acetate. The mixture was stirred 2.5 hr at room temperature, poured into ice water, extracted with ethyl acetate, washed with saturated sodium chloride solution and dried over anhydrous sodium sulfate. Filtration followed by evaporation of solvent provided an oil which was flash chromatographed on 20 g of silica gel (230–400 mesh) (eluent: 70% ethyl acetate/hexane 0.1% ammonium hydroxide). Concentration of the appropriate fractions provided an oil. Treatment of the oil with ethereal hydrogen provided under 0.245 g (61.3%) of product, as the hydrochloride, mp 154°–174°.

Analysis: Calculated for $C_{27}H_{43}NO_7HCl$: 59.38%C, 8.12%H, 2.57%N, Found: 58.82%C, 8.05%H, 2.74%N.

EXAMPLE 11

7β-Acetoxy-8,13-epoxy-1α-(t-butylamino)acetoxy-6β,9α-dihydroxylabd-14-en-11-one hydrochloride To a stirred solution of 106 mg of 7β-acetoxy-8,13-epoxy-1α,6β,9α-trihydroxylabd-14-en-11-one and 0.036 ml of dimethylaniline in 1 ml of dry dichloromethane in an ice bath was added dropwise a solution of 0.025 ml of bromoacetyl bromide in 1 ml of dry dichloromethane. The mixture was stirred 1 hr at ice bath temperature. The reaction mixture was allowed to warm to room temperature, diluted with ethyl acetate, poured onto ice/water, extracted with ethyl acetate, washed with cold sat sodium bicarbonate solution, water and dried over anhydrous sodium sulfate. Filtration followed by evaporation of the solvent provided an oil. The oil was dissolved in 1 ml of dichloromethane and added dropwise to a solution of 0.105 g of t-butylamine in 1 ml of ethyl acetate. The mixture was stirred at room temperature for 16 hrs, diluted with ethyl acetate, washed with water, sat sodium chloride solutions and dried over anhydrous sodium sulfate. Filtration followed by evaporation of the solvent provided an oil. The oil was purified by flash chromatography (230–400 mesh silica gel; eluent: 30% ethyl actate/hexane). Concentration of the appropriate fractions provided an oil, which was treated with ethereal hydrogen chloride, to provide 69.9 mg (48.3%) of product, as the hydrochloride, mp 165°–179°.

Analysis: Calculated for $C_{29}H_{45}NO_8HCl$: 60.04%C, 8.28%H, 2.50%N, Found: 59.73%C, 8.22%H, 2.26%N.

EXAMPLE 12

7β-Acetoxy-8,13-epoxy-1α-[2-(ethylamino)propionyloxy]-6β,9α-dihydroxylabd-14-en-11-one hydrochloride To a stirred solution of 1.0 g of 7β-acetoxy-8,13-epoxy-1α,6β,9α-trihydroxylabd-14-en-11-one in 10 ml of dichloromethane was added 0.35 ml of N,N-dimethylaniline. To the mixture was added slowly, by syringe, a solution of 0.30 ml (0.618 g) of bromopropionyl bromide in 10 ml of dichloromethane. The mixture was stirred 1 hr at room temperature, cooled in an ice-bath, poured into ice/water/sodium bicarbonate and the mixture was extracted with ethyl acetate. The extracts were washed with water, dried over anhydrous sodium sulfate, filtered and concentrated to an oil. The oil was dissolved in 10 ml of dichloromethane and added by syringe to a stirred solution of excess monoethylamine in 10 ml of ethyl acetate in an ice-bath. The solution was allowed to warm to room temperature and stirred for 3 hrs. The solution was poured into ice/water/ethyl acetate and extracted twice with ethyl acetate. The extracts were washed twice with water, with saturated sodium chloride solution, dried over anhydrous sodium sulfate and filtered. Filtration followed by evaporation of the solvent provided an oil. The oil was dissolved in a minimum volume of 2% methanol/dichloromethane and flash chromatographed on 150 g of silica gel (230–400 mesh). The column was eluted as follows: 1×400 ml 2% methanol/dichloromethane, 1×200 ml 2% methanol/dichloromethane, 3×100 ml 4% methanol/dichloromethane, 10×50 ml 4% methanol dichloromethane. A diasteriomer was contained in the first two 4% methanol/dichloromethane fractions. A mixture of diasteriomers was contained in the third 4% methanol/dichlormethane fraction. A second diasteriomer was contained in fractions 4 through 6. The diasteriomers were isolated. The diasteriomers were then combined, concentrated to an oil, dissolved in anhydrous ether and precipitated with ethereal hydrogen chloride to provide 0.354 g (26.6%) of product, mp 160°–174°.

Analysis: Calculated for $C_{27}H_{43}NO_8 \cdot HCl$: 59.38%C, 8.12%H, 2.57%N, Found: 59.00%C, 7.94%H, 2.39%N.

EXAMPLE 13

7β-Acetoxy-8,13-epoxy-1α-[2-(morpholin-4-yl)propionyloxy]-6β,9α-dihydroxylabd-14-en-11-one hydrochloride To a stirred solution of 0.3 g of 7β-acetoxy-8,13-epoxy-1α,6β,9α-trihydroxylabd-14-en-11-one in 3 ml of dichloromethane under nitrogen was added 0.106 ml of dimethylaniline. The solution was cooled to 0° and a solution of 0.090 ml of 2-bromopropionyl bromide in 3 ml of dichloromethane was added dropwise. The solution was stirred 1 hr at 0°, poured into ice/sodium bicarbonate/ethyl acetate and the mixture was extracted twice with ethyl acetate. The extracts were washed with water, dried over anhydrous sodium sulfate and filtered. Filtration followed by evaporation of solvent provided an oil. The oil was dissolved in 3 ml of dichloromethane and added to a stirred solution of 0.3 g of morpholine in 3 ml of ethyl acetate. The solution was stirred at room temperature for 3 hr., poured into water/ice/ethyl acetate and the mixture was extracted twice with ethyl acetate. The extracts were washed twice with water and once with sodium chloride solution. The solution was dried over anhydrous sodium sulfate, filtered and concentrated to an oil. The oil was dissolved in a minimum volume of 40% ethyl acetate/hexane and flash chromatographed on 150 g of silica gel (eluent: 10×50 ml of 40% ethyl acetate/hexane). Individual fractions were concentrated and the two diasteriomers were isolated. The fractions containing either diasteriomer were then combined and the solvent was evaporated. The resultant oil was dissolved in ether and precipitated with ethereal hydrogen chloride to provide, after drying, 0.121 g (28%) of product, mp 160°–170°.

Analysis: Calculated for $C_{29}H_{45}NO_9.HCl$: 59.22%C, 7.88%H, 2.38%N, Found: 59.53%C, 7.93%H, 2.17%N.

EXAMPLE 14

7β-Acetoxy-8,13-epoxy-1α-(4-methylpiperazin-1-yl)acetoxy-6β,9α-dihydroxylabd-14-en-11-one hydrochloride To a stirred solution of 300 ml of 7β-acetoxy-8,13-epoxy-1α,6β,9α-trihydroxylabd-14-en-11-one in 3 ml of dichloromethane containing 0.106 ml of dimethylaniline at 0° was added dropwise a solution of 0.075 ml (0.175 g) of bromoacetyl bromide in 3 ml of dichloromethane. The mixture was stirred 1 hr at 0°, poured into ice/saturated sodium bicarbonate solution/ethyl acetate, and the mixture was extracted with ethyl acetate. The extracts were washed with water, dried over anhydrous sodium sulfate and filtered. Filtration followed by evaporation of the solvent provided an oil. The oil was dissolved in dichloromethane and added to a solution of 0.3 g of N-methylpiperazine in 3 ml of ethyl acetate. The mixture was stirred 2 hrs. at room temperature, poured onto ice/water/ethyl acetate and the layers were separated. The extracts were washed with water, saturated sodium chloride solution and dried over anhydrous sodium sulfate. Filtration followed by evaporation of solvent provided an oil. The oil was dissolved in a minimum volume of 7% methanol/dichloromethane/0.1% ammonium hydroxide and flash chromatographed on silica gel (230–400 mesh), eluent: 7% methanol/dichloromethane/0.1% ammonium hydroxide, followed by 10% methanol/dichloromethane/0.1% ammonium hydroxide. Evaporation of solvent from the appropriate fractions provided an oil, which was dissolved in 5% ethyl acetate/ether and precipitated with ethereal hydrogen chloride to provide 0.242 g (56.3%) of product, mp 189°–196° dec.

Analysis: Calculated for $C_{29}H_{46}N_2O_8.HCl$: 59.32%C, 8.07%H, 4.77%N, Found: 59.12%C, 8.02%H, 4.77%N.

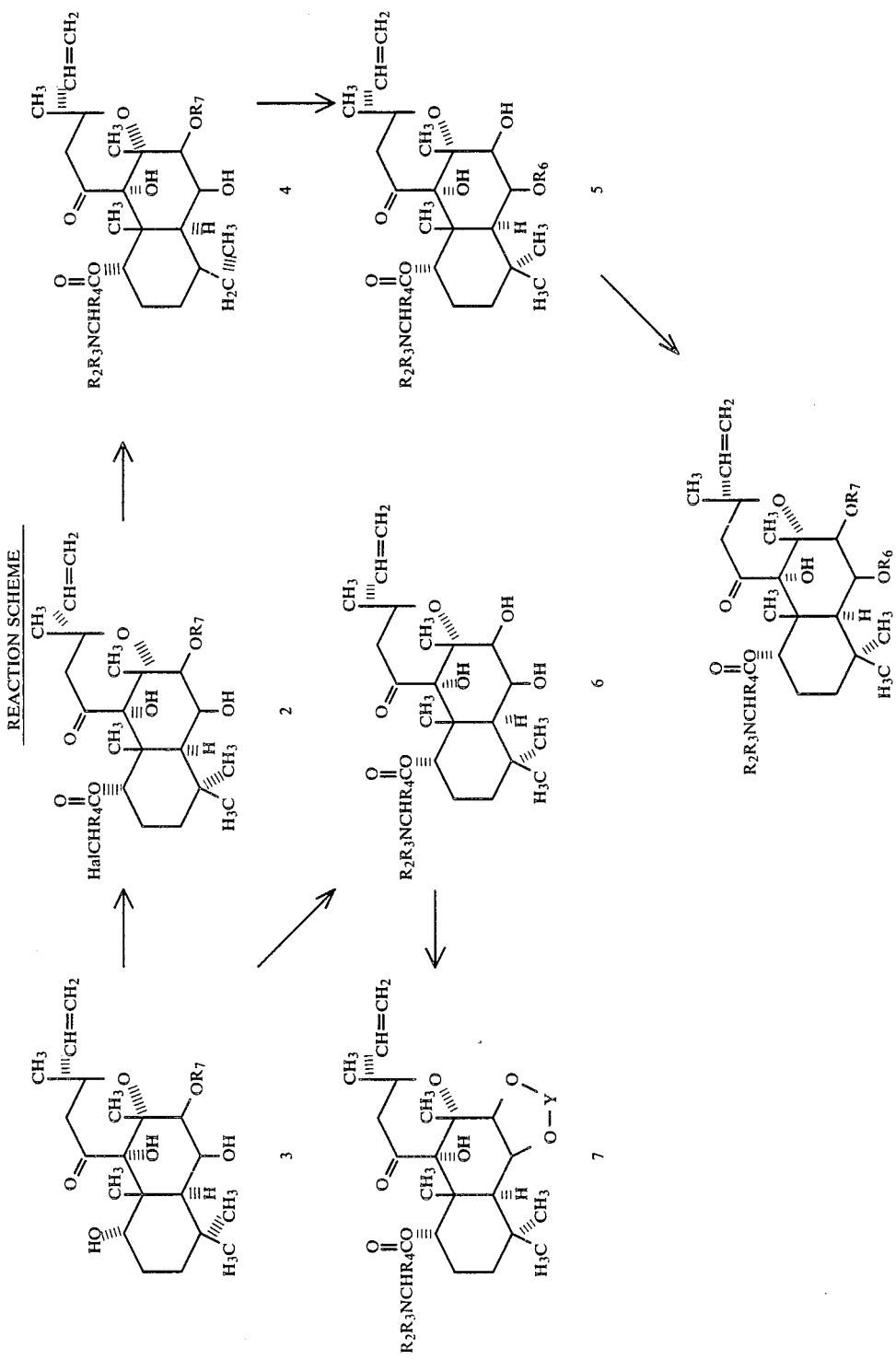
REACTION SCHEME
wherein $R_2$, $R_3$, $R_4$, $R_6$, $R_7$, Hal and Y are as hereinbeforedescribed.

We claim:

1. A compound of the formula

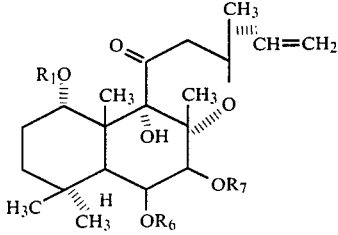

wherein $R_1$ is $R_2R_3NCHR_4CO$ wherein $R_2$ is hydrogen, loweralkyl or benzyl, $R_3$ is hydrogen or loweralkyl and $R_4$ is hydrogen, loweralkyl or benzyl; $R_2$ and $R_3$ taken together with the nitrogen atom to which they are attached form a group of the formula

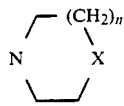

wherein X is CO, O, S, SO, $SO_2$; a group of the formula $CHR_9$ wherein $R_9$ is hydrogen, loweralkyl or a group of the formula $OR_{10}$ wherein $R_{10}$ is hydrogen or $COR_{11}$ wherein $R_{11}$ is loweralkyl; or a group of the formula $NR_{12}$ wherein $R_{12}$ is loweralkyl; n is 1 or 0; and $R_6$ and $R_7$ taken together form a group of the formula CO or SO; the optical and geometric isomers thereof, or a pharmaceutically acceptable acid addition salt thereof.

2. A compound according to claim 1 wherein $R_2$ and $R_3$ are hydrogen or loweralkyl.

3. A compound according to claim 1 wherein $R_2$ is hydrogen and $R_3$ is loweralkyl.

4. A compound according to claim 1 wherein $R_2$ and $R_3$ taken together with the nitrogen atom to which they are attached form a group of the formula

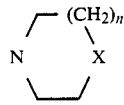

wherein X is CO, O, S, SO, $SO_2$, a group of the formula $CHR_9$ wherein $R_9$ is hydrogen, loweralkyl or a group of the formula $OR_{10}$ wherein $R_{10}$ is hydrogen or a group of the formula $COR_{11}$ wherein $R_{11}$ is loweralkyl, or a group of the formula $NR_{12}$ wherein $R_{12}$ is loweralkyl, and n is 0 or 1.

5. A compound according to claim 1 wherein $R_4$ is hydrogen or loweralkyl.

6. A compound according to claim 1 wherein $R_4$ is benzyl.

7. An intraocular pressure reducing composition comprising an inert adjuvant and as the active ingredient, an amount effective in reducing intraocular pressure of a compound of the formula

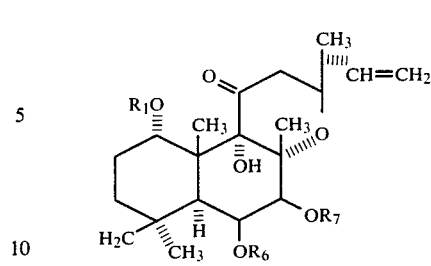

wherein $R_1$ is $R_2R_3NCHR_4CO$ wherein $R_2$ is hydrogen, loweralkyl or benzyl, $R_3$ is hydrogen or loweralkyl and $R_4$ is hydrogen, loweralkyl or benzyl; $R_2$ and $R_3$ taken together with the nitrogen atom to which they are attached form a group of the formula

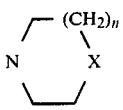

wherein X is CO, O, S, SO, $SO_2$, a group of the formula $CHR_9$ wherein $R_9$ is hydrogen, loweralkyl or a group of the formula $OR_{10}$ wherein $R_{10}$ is hydrogen or $COR_{11}$ wherein $R_{11}$ is loweralkyl, or a group of the formula $NR_{12}$ wherein $R_{12}$ is loweralkyl; n is 0 or 1; and $R_6$ and $R_7$ taken together form a group of the formula CO or SO; the optical and geometric isomers thereof or a pharmaceutically acceptable acid addition salt thereof.

8. A method of reducing intraocular pressure in mammals comprising administering to a mammal requiring intraocular pressure reduction an intraocular pressure reducing effective amount of a compound of the formula

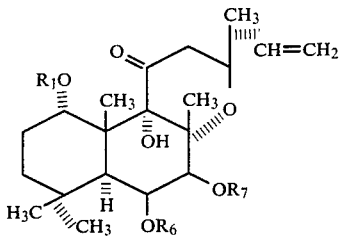

wherein $R_1$ is $R_2R_3NCHR_4CO$ wherein $R_2$ is hydrogen, loweralkyl or benzyl, $R_3$ is hydrogen or loweralkyl and $R_4$ is hydrogen, loweralkyl or benzyl; $R_2$ and $R_3$ taken together with the nitrogen atom to which they are attached form a group of the formula

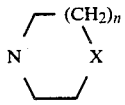

wherein X is CO, O, S, SO, $SO_2$, a group of the formula $CHR_9$ wherein $R_9$ is hydrogen, loweralkyl or a group of the formula $OR_{10}$ wherein $R_{10}$ is hydrogen or $COR_{11}$ wherein $R_{11}$ is loweralkyl, or a group of the formula $NR_{12}$ wherein $R_{12}$ is loweralkyl; n is 0 or 1; and $R_6$ and $R_7$ taken together form a group of the formula CO or SO; the optical and geometric isomers thereof or a pharmaceutically acceptable acid addition salt thereof.

* * * * *